United States Patent [19]

Lind et al.

[11] 4,204,532
[45] May 27, 1980

[54] NON-SKID FENESTRATION MATERIAL

[75] Inventors: Herbert C. Lind, Longmeadow, Mass.; Peter J. Rumore, Warehouse Point; Tadeusz S. Wysocki, Enfield, both of Conn.

[73] Assignee: The Dexter Corporation, Windsor Locks, Conn.

[21] Appl. No.: 841,029

[22] Filed: Oct. 11, 1977

[51] Int. Cl.² .............................................. A61F 13/00
[52] U.S. Cl. .................................. 128/132 D; 156/279; 428/198
[58] Field of Search .................... 128/132 D; 156/279; 428/147, 143

[56] References Cited

U.S. PATENT DOCUMENTS

| | | | |
|---|---|---|---|
| 2,793,136 | 5/1957 | Root | 428/147 |
| 3,030,251 | 4/1972 | LaBore et al. | 156/279 |
| 3,695,260 | 10/1972 | Endres | 128/132 D |
| 3,921,627 | 11/1975 | Wilson | 128/132 D |
| 3,930,497 | 1/1976 | Krebs et al. | 128/132 D |

Primary Examiner—Robert W. Michell
Assistant Examiner—M. Juten
Attorney, Agent, or Firm—Prutzman, Kalb, Chilton & Alix

[57] ABSTRACT

The present invention describes a non-skid fenestration sheet material for attachment to a disposable surgical drape. The sheet material comprising a fibrous base web impregnated with a fluid repellent material and having one planar surface adapted to be secured to the surgical drape and an exposed outer surface treated to provide an abrasion resistant non-skid character. These qualities are imparted to the outer surface by a random array of discrete resin droplet particles in the micron diameter range covering about 5% of the total planar surface area of said web. The resin particles are of intermediate film stiffness and are effective to frictionally resist sliding movement of surgical instruments and the like resting thereon even when the sheet material is inclined at an angle about 50° and more.

9 Claims, 1 Drawing Figure

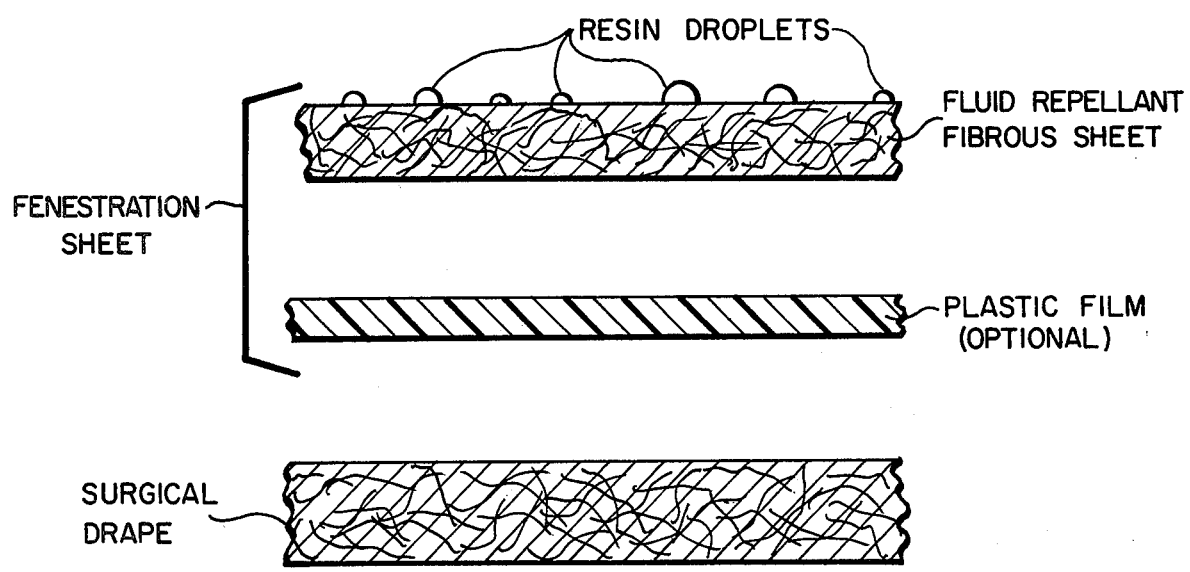

NON-SKID FENESTRATION MATERIAL

BACKGROUND AND SUMMARY OF THE INVENTION

The present invention relates generally to disposable surgical drapes and is more particularly concerned with a new and improved abrasion resistant nonwoven fenestration sheet material for attachment to a surgical drape and the like.

In recent years, disposable nonwoven materials have found increasingly greater application in hospitals, clinics and other medical facilities. One such disposable item is a surgical drape for covering the patient during an operative procedure. Typically the drape is cut or slit to provide an aperature or fenestration at the operative site. During a surgical procedure it is common practice of the surgeon to place surgical instruments and other implements on the surface of the drape adjacent the fenestration. Unfortunately, the surface of disposable nonwoven drapes will not retain the instruments in the position in which they are placed since the surface generally is too smooth to provide adequate gripping or holding characteristics. It has been suggested that a portion of the drape adjacent the fenestration be provided with a roughened surface, such as by heavy embossing, to prevent instrument slippage. However, such a construction has been found to be unsatisfactory.

To overcome the instrument slippage problem, several surgical drape manufacturers adhesively bond a foam material to the surgical drape at the fenestration area. The foam is usually backed by an impervious film which is adhesively bonded to the main drape material. Although the foam layer has provided substantial improvement with respect to the instrument slippage problem, it is by nature absorbent and tends to capture and retain body fluids immediately adjacent the surgical site. Typical examples of such foam materials can be found in the following U.S. Pat. Nos.: 3,668,050; 3,738,359; 3,763,857; and 3,930,497.

In accordance with the present invention, it has been found that substantially improved instrument retaining or non-skid characteristics can be achieved while eliminating the undesirable absorbency characteristic of the foam layer by replacing the foam with a skid resistant, water repellent layer of non-foam character. Accordingly, it is an object of the present invention to provide a new and improved fluid repellent fenestration sheet material that exhibits an improved frictional resistance to sliding movement of surgical instruments and the like resting thereon.

Another object of the present invention is to provide a new and improved non-skid fenestration material of the type described that fully replaces the foam layer with a water repellent fibrous sheet material provided with an abrasion resistant non-skid surface. Included in this object is the provision for a non-skid surface comprised of a random array of minute discrete solid droplets covering a minor portion of the total planar surface area of the fibrous sheet material.

Other objects will be in part obvious and in part pointed out more in detail hereinafter.

These and related objects are achieved in accordance with the present invention by providing a flexible fluid repellent fibrous sheet material well suited to being firmly secured to the top surface of a disposable surgical drape at an operative site fenestration. The fluid repellent sheet is provided with an exposed abrasion resistant non-skid outer surface comprised essentially of a random array of discrete solidified resin droplet particles of a size and character sufficient to effectively resist sliding movement of surgical instruments and the like placed thereon when the fenestration material is inclined at an angle greater than 40° relative to a horizontal plane.

A better understanding of the invention will be obtained from the following detailed description of the article and the desired features, properties, characteristics and relationships of elements set forth in the following description and illustratve embodiment.

The drawing illustrates in partially exploded cross-sectional view the resin droplets secured to a fibrous web attachable directly or by a plastic film to a surgial drape.

DESCRIPTION OF THE PREFERRED EMBODIMENT

As mentioned, the fenestration sheet material of the present invention provides a replacement for the foam layer utilized heretofore. Thus, before being adhesively laminated to a surgical drape material adjacent the fenestration, it is conventionally bonded to a thin film of plastic or the like which, in turn, is adhesively secured to the disposable surgical drape. However, the invention is not limited to such a multi-layer assembly and may be used separately or in combination with one or more other sheet-like materials.

The improved fenestration sheet consists essentially of a fluid repellent base sheet having one surface with an abrasion resistant non-skid character. The base sheet can take the form of a woven, nonwoven or spunbonded sheet material. If nonwoven, it may be either dry or wet laid, can be scrim reinforced and can contain a variety of natural or synthetic fibers. Generally, the preferred base sheet for a fenestration material is a water laid nonwoven fibrous web material typically containing 100% wood fibers. Accordingly, the remainder of this description will refer to such a base web for ease of understanding.

The fibrous base web is treated with a suitable fluid repellent agent, which treatment may take place either during or after fabrication. The fluid repellent treatment should be of a type that will permit sterilization of the resultant fenestration sheet either by means of ethylene oxide, steam, gamma rays or comparable sterilizing processes acceptable to the medical industry. In the preferred embodiment, the desired repellency is achieved by utilizing a fluorochemical treating agent commercially available to the paper industry. In this connection, it has been found that excellent results are achieved by using a fluorinated polymer treating agent that has been used commercially for treating surgical drapes and surgeons' gowns to prevent penetration of water, body fluids, disinfectants and other liquids. One such material which has found acceptance in the nonwoven industry is the "Scotchban" brand fluorochemical treating agent sold under the designation "FC-824" by Minnesota Mining and Manufacturing Company. This fluid repellent treatment also typically includes the incorporation of anti-static agents, extenders such as supplementary water repellent agents, buffers and the like and conveniently is applied by passing the nonwoven fibrous base sheet through an aqueous emulsion of the repellent and subsequently drying the sheet. A typical aqueous emulsion treating formulation would contain about 0.7 to 1.5 parts by volume of FC-824 concentrate as received with each 100 parts of water and would be used at a treating bath temperature of about 120°–150° F.

As will be appreciated from the foregoing, the preferred nonwoven sheet material used for the non-skid fenestration sheet can consist of simply a light weight version of a typical surgical drape material, although other nonwoven or woven materials may readily be employed. In accordance with the present invention, the abrasion resistant non-skid surface is applied to the light-weight water repellent fibrous base web in the form of minute droplet particles of a synthetic or natural polymeric material, the particles preferably being applied in the form of a spray to provide a polymer pick-up of about 5 to 10% by weight uniformly over one entire surface of the base sheet material and a surface coverage of at least 2% but less than 10% of the total planar surface area.

Although an airless spray technique has been used effectively to provide the desired droplet particle size and surface coverage, other latex application techniques may also be employed to impart the non-skid characteristics to the outer surface of the fenestration material. For example, size press, reverse roll cover and print bonding are all acceptable alternative methods of latex resin application and could be utilized provided they can obtain the desired latex particle size and coverage found most effective in achieving the non-skid characteristics of the present invention.

As will be appreciated, the preferred spray technique will result in a random array of discrete latex resin droplet particles of varied size and location over the entire surface of the nonwoven sheet material. The particles may be as small as 1 micron in diameter or as large as 1,000 microns. However, it has been found that excellent results are achieved when the particle size varies from about 10 to 500 microns, with the predominant particle size being in the area of 50 to 150 microns.

As will be appreciated, variation of droplet size will depend on the spray technique employed and will affect the total surface coverage that is achieved. In this connection, it has been found that improved non-skid characteristics can be achieved with a surface area coverage as low as about 2%, with little gain in anti-skid properties being achieved when the coverage exceeds 10%. Thus, a convenient operating range is between 2% and 9% coverage of the surface area, with a typical average coverage being about 5%. As will be appreciated, it is generally preferred to utilize as little resin as possible for economical reasons and, consequently, a preferred operating range for resin coverage is between about 2.5% and 6%.

As an example, a sample taken from a commercial grade of material made in accordance with the present invention was stained with a dye and color photographs were taken of three random areas. The area of the resin drops were measured under a stereo microscope and compared to the total area of the photographs to determine the present resin droplet coverage. The results were:

| Sample | Resin Coverage (%) |
|--------|--------------------|
| 1      | 4.36               |
| 2      | 2.48               |
| 3      | 2.81               |
| Ave.   | 3.23               |

The same material was examined for particle size distribution and revealed a minimum size of 30 microns, a maximum size of 459 microns and a mean sample value of 124 microns.

It is important that the latex droplet spray provide not only a non-skid surface on the nonwoven sheet material but also that the surface be sufficiently abrasion resistant to resist "pilling" of the surface during use. This is necessary since the fenestration sheet material is in such close proximity to the surgical site that it must withstand abrasive rubbing by the surgeon's gown, the instruments, or any other material coming thereagainst. As will be appreciated, even slight linting, fuzzing or the like might contaminate the surgical site. Accordingly, it is necessary to utilize a resin material of a type that is soft enough to resist instrument slippage yet hard enough to exhibit good abrasion resistance. In this connection, it has been noted that the soft styrene butadiene resins are not desirable as they fail to provide the desired abrasion resistance and also exhibit yellowing upon aging. On the other hand, acrylic and/or polyurethane emulsions of intermediate film hardness, that is, having a film stiffness range as measured by their temperature of crystallization of between −47° C and +33° C have been found acceptable. The temperature of crystallization ($T^c{}_{300}$) is the temperature at which the torsional modulus of an air dried film is 300kg/cm$^2$. In this connection, the acrylic emulsions that exhibit a film stiffness range between −14° C and +17° C have been found to provide the best compromise between the desired non-skid and abrasion resistance properties. Among these, it has been found that the resins having film stiffness values of about −14° C and −7° C provide the best balance and are therefore preferred for the fenestration end use application.

While the invention should not be limited to any specific materials, it has been found that best results are achieved with using acrylic-ester latex emulsions sold by Rohm and Haas under the trade designations Rhoplex HA- 8 and Rhoplex HA-24 as well as blends thereof. Thus, in general, the very hard polymeric films are avoided since they tend to enhance instrument slippage, as are the very soft resins that lack abrasion resistance. Thus, latex material which form intermediate film properties are preferred. As mentioned hereinbefore, the materials employed also should be capable of withstanding sterilization techniques utilized for materials having medical application. It will be appreciated, of course, that the latex droplets should be applied to the nonwoven base sheet material as uniformly as possible on only one side of the sheet.

The treated fenestration material is dried after application of the latex spray and may, if desired, be subjected to a crimping or micro-compacting operation either before or after application of the non-skid droplets thereto.

As a further measure of the abrasion resistance of the material made in accordance with the present invention, it has been found that the material should be capable of withstanding at least 5 cycles, and preferably 10 cycles and more, of the abrasion resistance test procedure set forth in Section 4.3.2 of the military specification designated MIL-F-36901A dated June 3, 1974. That procedure utilizes a Stoll Quartermaster Abrasion Tester with Frosting Attachment and a Lytrol finished abrading cloth. In accordance with the test procedure, a fresh sample of the Lytrol finished cloth having dimensions of 3" to 10" is secured to the face of the top plate of the abrasion tester. The fenestration material to be tested is cut into a 5" square and fastened on the foam pad of the tester's bottom plate. A 2½ lb. weight is applied to the top plate, and the Lytrol finished cloth is brought into contact with the sample to be tested. The tester is activated, and the sample is inspected after every five cycles for the first thirty cycles, and after every ten cycles beyond thirty cycles until the sample fails. If a failure has not occured after 70 cycles, the test is terminated.

Test results are reported as the number of cycles when pilling is first observed, with "pilling" being defined as the breaking off of particles or fibers which start to form clumps or beads.

As mentioned, a primary advantageous feature of the fenestration sheet material of the present invention is its ability to resist the sliding, slipping or skidding action of surgical instruments across the surface thereof. The non-foam materials utilized heretofore have relatively poor slippage resistance when compared to the foam laminates. Using the inclined plane test for skid resistance, the prior non-foam material evidenced a slippage angle of about 20° as compared with an angle of about 40°-50° for foam material. The inclined plane test is relatively simple and involves placing the material to be tested on a flat, smooth surface that can be tilted. A stainless steel surgical towel clamp is placed on the test material and the support is tilted until the instrument begins to slip along the test material. The angular displacement of the support from the horizontal plane is noted and recorded as the slippage angle.

The fenestration material of the present invention equals and exceeds the slippage angle of foam materials while avoiding the undesirable fluid absorbency of foam materials. The slippage angle of this material is at least 40° and can be as high as 80° for the softer resin droplet materials. Generally, the preferred material has a slippage angle of about 40°-65° with a value of 45°-55° being typical.

In order that the present invention may be more readily understood, it will be further described with reference to the following specific example which is given by way of illustration only and is not intended to be a limit on the practice of the invention.

EXAMPLE I

A 100% wood fiber nonwoven web material having a basis weight of 52.5g/m$^2$ was formed on commercial papermaking machinery and was saturated with an aqueous solution of a fluorochemical water repellent (FC-824) prior to passing through a first drying cycle. The sheet material was then subject to a fine airless spray of an acrylic latex emulsion having a $T_{300}{}^c$ of $-7°$ (Rhoplex HA-24) to provide a resin pick-up of about 8% by weight and a surface coverage of about 5%.

The resultant material exhibited a Finch tear of 3,242 grams, an Instron dry tensile strength of 2,987 grams per 25 mm, a dry toughness of 27.7 cm/gm/cm$^2$ and a dry mullen of 1,019 g/cm. Samples of the resultant sheet material were tested for their non-skid character. Using the inclined plane test, and average slippage angle of 48° was measured.

The material was also tested for abrasion resistance in accordance with test procedure 4.3.2 of MIL-F-36901A. The abrasion test was conducted under both dry and wet conditions up to 70 cycles, the wet conditions resulting from treatment of the test material with a 0.9% saline solution. Under both dry and wet conditions, no visible pilling was noted after 70 cycles, and under dry conditions, some lint from only the Lytrol finishing cloth was observed after 50 cycles. Accordingly, the test was repeated by replacing the Lytrol finishing cloth with the fenestration test material so that the test material was abraded against itself. In this instance, no pilling or lint was visible under dry or wet conditions after 70 cycles.

EXAMPLE II

The identical procedure of Example I was followed using the same materials except that a pilot plant papermaking machine was used. The resultant web material had a basis weight of 51.6g/m$^2$ and comparable paper properties. Samples of this material were found to exhibit an average slippage angle of 60°. The abrasion resistance test showed no pilling after 50 cycles and very slight pilling starting after 70 cycles when the material was wet. Under dry conditions no pilling was noted after 30 cycles but pilling was evidenced after 50 cycles.

As will be apparent to persons skilled in the art, various modifications, adaptations and variations of the foregoing specific disclosure can be made without departing from the teaching of the present invention.

We claim:

1. A non-skid fenestration sheet material for attachment to a disposable surgical drape having a fenestration comprising a flexible, light weight, fluid repellent, fibrous web having an inner planar surface for overlying the surgical drape in confronting relationship thereto and for being firmly secured to the surgical drape and an exposed abrasion-resistant non-skid outer surface comprised essentially of a random array of discrete resin droplet particles forming a discontinuous layer covering more than 2% and less than 10% of the total planar surface area of said exposed outer surface, said particles having exposed surfaces characteristic of droplets and an average particle size of less than 1000 microns, said resin particles being of intermediate film stiffness and effective to frictionally resist sliding movement of instruments and the like resting thereon even when said outer surface is inclined at an angle greater than 40° to a horizontal plane.

2. The fenestration sheet material of claim 1 wherein said outer surface exhibits a skid resistance angle of up to about 80° and an abrasion resistance of greater than 5 cycles when tested in accordance with MIL-F-3690A.

3. The fenestration sheet material of claim 1 wherein said resin droplet particles have a temperature of crystallization in the range of $-47°$ C to 33° C at a torsional modulus of 300kg/cm$^2$.

4. The fenestration sheet material of claim 1 wherein said resin droplet particles cover between about 2.5% and 6% of the surface area of said outer surface.

5. The fenestration sheet material of claim 1 wherein said droplet particles have a film stiffness range between about $-14°$ C and 17° C.

6. The fenestration sheet material of claim 1 wherein said resin droplets are formed from an acrylic latex emulsion, said droplets uniformly covering said outer surface and providing said sheet material with a slippage angle of 45° and more.

7. The fenestration sheet material of claim 1 wherein said fibrous web is a water-laid nonwoven web impregnated with a fluid repellent fluorinated polymer.

8. The fenestration sheet material of claim 1 wherein said outer surface exhibits a pilling-free abrasion resistance of more than 10 cycles.

9. The fenestration sheet material of claim 1 wherein said resin is an acrylic resin having a film stiffness of about −7° C and said non-skid surface has a slippage angle of 40°–65° and an abrasion resistance greater than 30 cycles.

* * * * *